United States Patent [19]

Naumann et al.

[11] 4,243,553

[45] Jan. 6, 1981

[54] PRODUCTION OF IMPROVED MOLYBDENUM DISULFIDE CATALYSTS

[75] Inventors: Alfred W. Naumann, Charleston, W. Va.; Albert S. Behan, Bronxville, N.Y.

[73] Assignee: Union Carbide Corporation, New York, N.Y.

[21] Appl. No.: 47,238

[22] Filed: Jun. 11, 1979

[51] Int. Cl.$^3$ .................. B01J 27/02; B01J 27/24; B01J 31/12; C01G 37/00

[52] U.S. Cl. .................. 252/439; 252/438; 252/431 N; 423/53

[58] Field of Search .............. 252/438, 439, 431 N; 423/53

[56] References Cited

U.S. PATENT DOCUMENTS

| | | | |
|---|---|---|---|
| 2,112,292 | 3/1938 | Jones | 423/53 X |
| 2,367,946 | 1/1945 | Kaercher | 423/53 |
| 2,490,488 | 12/1949 | Stewart | 260/449.6 |
| 2,686,763 | 8/1954 | Johnson et al. | 252/439 X |
| 3,156,420 | 11/1964 | Growl | 252/25 X |
| 3,390,080 | 6/1968 | Groszek et al. | 252/25 |
| 3,876,755 | 10/1973 | Kurtak et al. | 423/56 |
| 4,098,839 | 7/1978 | Wilms et al. | 252/439 X |
| 4,151,191 | 4/1979 | Happel et al. | 252/439 X |

FOREIGN PATENT DOCUMENTS

| | | | |
|---|---|---|---|
| 1473900 | 3/1967 | France | 252/439 |
| 7603197 | 3/1976 | Netherlands | 252/439 |

OTHER PUBLICATIONS

Sulphide Catalysts Their Properties and Applications, Otto Weisser and Stanish Landk, Pergamon Press, 1973, p. 57, printed in Czechoslovakia.

"Thermal Decomp. of $(NH_4)_2MoO_2S_2$", T. P. Rosak et al., J. Inorg. Chem., 1973, vol. 35, pp. 1895–1904.

Mills & Steffgen Cat. Rev. 8, 159 (1973).

"Nobel Metals, Mo & W in Hydrocarbon Synthesis", Shultz et al., report 6974, Jul. 1967, Bu. of Mines.

Angew, Chem. Int. Ed. Engl. 17, 279, 535 (1978).

*Primary Examiner*—Delbert E. Gantz
*Assistant Examiner*—William G. Wright
*Attorney, Agent, or Firm*—Harrie M. Humphreys

[57] ABSTRACT

High surface area molybdenum disulfide, $MoS_2$, is produced by the thermal decomposition of selected substituted ammonium thiomolybdate salts at temperatures of about 300°–800° C., with said salts being heated to decomposition temperature slowly, in an essentially oxygen-free atmosphere, through the temperature interval in which the substantial portion of the particular substituted ammonium thiomolybdate salts decompose. The product molybdenum disulfide has superior catalytic properties for the water gas shift and methanation reactions compared with conventional $MoS_2$. The stability of the catalyst is enhanced by decomposing the thiomolybdate salt in admixture with an inert, preformed particulate diluent or by bulk doping said salt with tungsten or vanadium prior to decomposition of the salt. The molybdenum disulfide of the invention also has desirable properties for use in catalyzed hydrogenation and hydrotreating reactions, i.e., hydrodenitrogenation and hydrodesulfurization reactions, particularly when employed in nickel or cobalt-promoted form.

30 Claims, No Drawings

PRODUCTION OF IMPROVED MOLYBDENUM DISULFIDE CATALYSTS

BACKGROUND OF THE INVENTION

1. Field of the Invention

The invention relates to molybdenum disulfide catalysts. More particularly, it relates to the preparation of such catalysts having enhanced catalytic properties.

2. Description of the Prior Art

The catalytic hydrogenation of carbon monoxide to form methane is a well known, established methanation reaction. This reaction:

$$CO + 3H_2 \rightarrow CH_4 + H_2O, \tag{1}$$

utilizes a synthesis gas, as from the gasification of coal with oxygen and steam. Prior to methanation, the gas stream is commonly treated to provide a desired $H_2/CO$ ratio and to remove excess $CO_2$ and deleterious impurities such as sulfur impurities. As the $H_2/CO$ ratio of the raw synthesis gas is generally substantially below the necessary minimum ratio of 3/1, at least a portion of the carbon monoxide is generally first reacted with steam, over an iron or other suitable catalyst in the well-known "water gas shift" reaction as follows:

$$CO + H_2O \rightarrow CO_2 + H_2. \tag{2}$$

Excessive $CO_2$ in the gas stream is removed by conventional means, such as by treatment with alkaline absorbents. Sulfur impurities are also removed to substantially under 5 ppm, e.g. to less than about 1 ppm, preferably to less than 0.2 ppm, to protect the methanation catalyst from poisoning by such sulfur impurities. Hydrogen sulfide or other sulfur bearing gases are absorbed, selectively or non-selectively, by the absorben employed for carbon dioxide removal. When necessary, final cleanup may be accomplished by passing the gas stream through iron oxide, zinc oxide or activated carbon to remove residual traces of $H_2S$ or organic sulfides.

In view of the diminishing supply of natural gas, such methanation techniques are of considerable interest in the art as a means for producing substitute natural gas (SNG) from coal, shale oil, tar sands, petroleum residues, biomass, industrial and municipal waste, and other complex carbonaceous material. While a variety of specific processing techniques for SNG production have been proposed in the art, essentially all of these techniques provide for the steps of (1) gasification, to produce crude mixtures of CO, $H_2$, $CO_2$, $H_2O$, $CH_4$ and other trace components; (2) catalytic water gas shift to adjust the $CO:H_2$ ratio as indicated above; (3) and catalytic methanation in accordance with reaction (1) above and related reactions that might occur, such as:

$$CO_2 + 4H_2 \rightarrow CH_4 + 2H_2O \text{ and/or} \tag{3}$$

$$2CO + 2H_2 \rightarrow CH_4 + CO_2. \tag{4}$$

The methanation catalysts currently being seriously considered for commercialization are based on nickel or cobalt as the active ingredient. These metallic catalysts are very active, selective and relatively cheap. They are, however, extremely sensitive to poisoning by sulfur compounds. Since almost all of the carbonaceous feeds employed for synthesis gas production contain sulfur that is converted largely to $H_2S$ during the initial gasification step, costly acid gas purification operations must be included in SNG process designs so as to lower the $H_2S$ level to the fractional ppm level indicated above to achieve commercially feasible, long catalyst life. It would be highly desirable in the art, therefore, if sulfur-resistant methanation catalysts were commercially available as this would permit a considerable reduction in the degree of gas purification processing required prior to the methanation step in SNG production operations. If such a catalyst would also catalyze water shift reaction (2) effectively, the number of individual processing steps, and the overall cost of SNG production could be even further reduced.

It has long been recognized in the art that molybdenum sulfide, $MoS_2$, and tungsten sulfide, $WS_2$, as well as more complex mixed sulfides, are sulfur-tolerant methanation catalysts. $MoS_2$ occurs native as molybdenite and can be prepared artifically by heating molybdenum dioxide, molybdenum trioxide or ammonium molybdate in $H_2S$ or sulfur vapor. Thus, Mills and Steffgen, in Catalyst Rev. 8, 159 (1973), review the results of several studies with molybdenum and tungsten sulfide methanation catalysts prepared in a variety of ways. Even the best of these catalysts were only moderately active. In the Stewart patent, U.S. Pat. No. 2,490,488, $MoS_2$ catalysts modified by the addition of alkali metal compounds are disclosed as shifting the hydrocarbon synthesis of synthesis gas from methane to a mixture of higher molecular weight products. A CO conversion of 95% was achieved at 280° C. and 200 psig, at a commercially impractical space velocity (SV) of 86 $hr^{-1}$. A temperature of 410° C. was required to achieve 98% conversion at an SV of 100 $hr^{-1}$.

Methanation activity for molybdenum catalysts, including those prepared as sulfides, was reported by Schultz et al, U.S. Bureau of Mines, Rep. Invest. No. 6974 (1967). In the preparation of catalyst L 6135, $H_2S$ gas and an aqueous solution of aluminum nitrate were added to an ammoniacal aqueous solution of ammonium molybdate to precipitate a mixture of ammonium thiomolybdate and hydrated aluminum hydroxide. This coprecipitate was reduced in $H_2$ before use. When employed with a stream having a $CO:H_2$ ratio of 1:3 at 400° C., the CO conversion was 47.6% at a space velocity of only 295 $hr^{-1}$. Shultz et al also prepared catalysts by impregnating silica-alumina or activated carbon supports with ammonium molybdate, followed by calcining, to give a supported molybdenum oxide for which a conversion of 76.6% was reported at 420° C. and 21 atm. This catalyst was not sulfided. Other catalysts prepared as oxides by coprecipitating aluminum and molybdate salts, without sulfiding, provided methanation performance similar to that of impregnated materials.

Such previously available molybdenum methanation catalysts, including $MoS_2$ catalyst materials, are relatively inactive, and are not generally considered to possess sufficient activity to justify use in commercial operations. Despite the desirable sulfur resistant properties of $MoS_2$ materials, therefore, such available materials have not been suitable for practical use in providing synthetic natural gas to meet existing and anticipated requirements for low-cost, high BTU gaseous heating fuels.

There remains a need in the art, therefore, for an improved methanation catalyst having an acceptable degree of activity for use in commercial operations, coupled with an absence of the extreme sensitivity to poisoning by sulfur compounds that is characteristic of the active nickel and cobalt catalyst compositions. The satisfactory catalytic activity and the reduced acid gas purification requirements thus achieved would enable the overall SNG production operations to be carried out in a manner enhancing, on an overall technical-economic basis, the production of low-cost, high purity SNG as a replacement for natural gas.

It is an object of the invention, therefore, to provide an improved, sulfur-resistant methanation catalyst.

It is another object of the invention to provide a sulfur-resistant molybdenum disulfide catalyst of improved catalytic activity.

It is another object of the invention to provide a process for the production of an improved molybdenum disulfide catalyst.

It is a further object of the invention to provide an improved molybdenum disulfide catalyst capable of enhancing the overall operation for the production of SNG.

With these and other objects in mind, the invention is hereinafter disclosed in detail, the novel features thereof being particularly pointed out in the appended claims.

SUMMARY OF THE INVENTION

High surface area molybdenum disulfide is produced by thermally decomposing a substituted ammonium thiomolybdate salt having the formula $B_2[MoO_xS_{4-x}]$, where B is a substituted aliphatic ammonium ion or a cyclic amine containing one or more basic N atoms, and x is 0, 1 or 2. Decomposition is carried out at temperatures of about 300°–800° C., preferably at about 400°–500° C., with the thiomolybdate salt being heated to the decomposition temperature so that a very slow heating rate, in an essentially oxygen-free atmosphere, is employed in the fairly narrow temperature interval in which the substantial portion of the particular substituted thiomolybdate salt decomposes. The $MoS_2$ of the invention can advantageously be employed as a water gas shift and/or methanation catalyst, and for us, particularly in nickel or cobalt promoted form, for catalyzing hydrogenation or hydrotreating reactions.

DETAILED DESCRIPTION OF THE INVENTION

The objects of the invention are accomplished by a novel process for the preparation of molybdenum disulfide, $MoS_2$, having desirable properties for use as a methanation catalyst in addition to the sulfur resistant characteristics commonly associated with molybdenum disulfide. Previously available $MoS_2$, as indicated above, does not have sufficient activity to warrant its consideration, on an overall technical and economic basis, as a methanation catalyst, in commercially feasible SNG operations.

The present invention relates to the thermal decomposition of a selected substituted ammonium thiomolybdate salt under specific decomposition conditions to produce a $MoS_2$ catalyst material having desirable properties for water gas shift, methanation and other catalyst applications. The thiomolybdate salt has the formula $B_2[MoO_xS_{4-x}]$, where B is a substituted aliphatic ammonium ion containing from one to four alkyl groups or a cyclic amine containing one or more basic N atoms, and x is 0, 1 or 2. Illustrative examples of said substitutes aliphatic ammonium ions are those containing one alkyl group, such as where $B^+$ is $n-C_4H_9NH_3^+$, two alkyl groups, e.g., where $B^+$ is $(C_2H_5)_2NH_2^+$, three alkyl groups, e.g., where $B^+$ is $(CH_3)_3NH^+$ and four alkyl groups, e.g., where $B^+$ is $(CH_3)_4N^+$. Among the suitable thiomolybdate salts of this type utilized in the practice of the invention are (n-Butylamine)$_2$ $H_2MoS_4$, (Diethylamine)$_2$ $H_2MoS_4$, and tetramethyl ammonium thiomolybdate, $[(CH_3)_4N]_2$ $MoS_4$.

Among the suitable thiomolybdate salts in which B is the cation of a cyclic amine are those in which B contains one basic N atom, e.g., the piperidinium cation derived from piperidine and the pyrrolidinium cation derived from pyrrolidine, and in which B contains more than one basic N atom, e.g., the piperazinium cation derived from piperazine and the hexamethylenetetramonium cation derived from hexamethylenetetramine. Illustrative examples of amine thiomolybdates suitable for use as starting materials in the process of the invention include piperazinium thiomolybdate, $(C_4H_{10}N_2)$ $H_2MoS_4$; piperazinium oxythiomolybdate, $(C_4H_{10}N_2)$ $H_2Mo$ $OS_3$; hexamethylenetetramine thiomolybdate, $(C_6H_{12}N_4)_4.(NH_3)_4.(H_2MoS_4)_3$; piperidine thiomolybdate, $(C_5H_{11}N)_2$ $H_2MoS_4$.

Those skilled in the art will appreciate that the substituted ammonium thiomolybdate salts suitable as the starting materials for use in the practice of the invention are known materials that can be prepared by synthesis techniques reported in the art. Such synthesis techniques do not form an essential part of the invention, which is directed to the production of improved $MoS_2$ catalyst materials by the decomposition of such known substituted ammonium thiomolybdate salts under the carefully controlled conditions herein disclosed and claimed. It will also be appreciated that other substituted ammonium thiomolybdate salts of the type herein described, apart from those referred to herein, may exist and also constitute suitable starting materials for use in the practice of the invention. It will be understood, however, that not all such substituted ammonium thiomolybdate salts of the type described, whether presently available or that hereinafter become available in the art, will be suitable or desirable for practical use as a starting material in the $MoS_2$ process of the invention.

Thermal decomposition of unsubstituted ammonium thiomolybdate salts have been reported in the J. Inorg. Nucl. Chemistry, 35, 1895–1904 (1973), with the thermal decomposition of $(NH_4)_2$ $MoO_2S_2$, $(NH_4)_2$ $MoS_4$, $(NH_4)_2$ $WO_2S_2$ and $(NH_4)_2$ $WS_4$, being disclosed, in accordance with available analytical techniques using a Mettler instrument and a DTA/TGA instrument of Linseis KG, West Germany. The experiments were carried out under nitrogen atmosphere at normal pressure employing a heating rate of 6° C./min., a heating rate of 6°–10° C./min. being conventional for such analytical procedures. At a decomposition temperature of 400° C. $MoS_2$ was reported as the probable composition. Such analytical procedures did not, however, relate to the potential advantages and disadvantages of $MoS_2$ as a methanation catalyst.

The invention herein disclosed and claimed, on the other hand, is directed to a process for producing a novel $MoS_2$ catalyst product having commercial application by the thermal decomposition of selected substituted ammonium thiomolybdate salts under controlled conditions. As a result, a form of bulk, high surface area molybdenum disulfide is formed that has superior catalytic properties for the water gas shift and methanation reactions compared with previously described $MoS_2$ catalysts prepared by previously known methods.

The substituted ammonium thiomolybdate salts are decomposed, in the practice of the invention, at a decomposition temperature of from about 300° C. to about 800° C., preferably at a temperature of from about 400° C. to about 500° C. Contrary to the standard heating rate of 6°–10° C./min. for the conventional analytical decomposition technique referred to above, it has been found that molybdenum disulfide, $MoS_2$, having improved catalytic properties, is obtained when decomposition of the indicated substituted thiomolybdate salts, conveniently in the form of small pressed pellets rather than loose powder, is carried out by heating the salt very slowly through the temperature interval in which a major or substantial portion of the substituted thiomolybdate salt decomposes. This temperature interval in which very slow heating is required comprises a fairly narrow temperature range that will vary depending on the particular substituted thiomolybdate salt being decomposed in any given application of the invention. The temperature interval for any particular salt can readily be determined by heating the salt to the decomposition range indicated above and observing the fairly narrow temperature range during the course of such heating over which the major portion of the decomposition of the salt occurs. In the decomposition of 2/1 piperazinium thiomolybdate, for example, very slow heating is employed through the temperature range of from about 100° C. to about 200° C. in which a substantial portion of the salt decomposes. It should be noted that particular care must be taken to assure that decomposition through the indicated temperature interval of substantial decomposition is carried out in an essentially oxygen-free atmosphere. Such decomposition has been found to be advantageously carried out under vacuum in specific applications of the invention although other conventional means for maintaining an essentially oxygen-free atmosphere may be preferable in commercial operations. It is within the scope of the invention, for example, to employ a nitrogen or argon atmosphere and to have hydrogen present within the range of from about 0 to 100% by volume based on the total volume of essentially oxygen-free atmosphere in the decomposition kiln or zone employed, conveniently with such hydrogen present in amounts up to about 10% by volume. As noted above, however, the use of a nitrogen or argon or hydrogen atmosphere, e.g., conveniently with such hydrogen present in amounts up to about 10% by volume. As noted above, however, the use of a nitrogen or argon or hydrogen atmosphere, e.g., conveniently supplied by forming gas, must be carefully controlled to assure that the atmosphere is essentially oxygen-free as is achieved in other embodiments by carrying out the decomposition under vacuum.

In the practice of the invention on a laboratory scale, it was found that decomposition of the indicated substituted thiomolybdate salts is advantageously carried out by heating the salts at a rate of from about 0.5° to about 2° C./min. through the temperature interval in which a major or substantial portion of the substituted thiomolybdate salt decomposes. It will be appreciated by those skilled in the art that, in commercial applications of the invention, operations outside this narrow range may be permissible because of the particular characteristics and performance capability of the particular kiln or other decomposition apparatus employed in practical commercial-scale operations. Very slow heating of the particular substituted thiomolybdate salt through the temperature range of substantial decomposition should be observed in any event, whether within the observed range of from about 0.5° to about 2° C./min. or such other slow heating rate as may pertain to any given commercial application of the invention. Higher heating rates can be employed at temperatures both below and above the narrow temperature interval at which decomposition of the salt essentially occurs. By carrying out the preheating of the indicated salts at such slow rates, the $MoS_2$ product is found to have the desirable catalytic properties indicated above, whereas heating the same salts at conventional rates does not result in such beneficial results to the same desirable extent.

Upon carrying out the decomposition of the selected substituted ammonium thiomolybdate salts in an essentially oxygen-free atmosphere at the slow heating rate hereinabove indicated, the product molybdenum disulfide is obtained as a high surface area product having desirable catalytic properties. The $MoS_2$ product will thus have a surface area of from about 25 to about 150 $m^2/gm$. It should be noted, however, that the high surface area is a factor, but only one factor, in the improved catalytic properties resulting from the production of $MoS_2$ in accordance with the present invention. The improved properties result, to the contrary, from the particular decomposition conditions employed with the particular substituted ammonium thiomolybdate salts disclosed herein. Such conditions result in the production of an active $MoS_2$ catalytic product that is obtained in bulk, high surface area form. The decomposition conditions of the invention do not result in improved catalytic properties of $MoS_2$ product from all thiomolybdate salts, however, but expectedly achieve such results with those herein disclosed as falling within the scope of the invention.

In the preparation of substituted ammonium thiomolybdate salts for trials carried out in the practice of the invention, solutions containing 200 g of ammonium paramolybdate (APM) and approximately three moles of the appropriate amine in 1 l of water were treated with gaseous hydrogen sulfide. The mixtures were digested at 65°–85° C. until there was no observable further consumption of hydrogen sulfide, typically about 1–3 hours. The mixtures were then cooled to room temperature or below using an ice bath. The precipitates that formed were collected by filtration, rinsed with denatured alcohol, and dried in air at room temperature. In general, the differences between the observed and calculated values for the formulas of the substituted ammonium thiomolybdates were well within the ±0.5% estimated uncertainties of the Mo,S and C analyses and the ±0.3% estimated uncertainties of the N and H analyses.

When employing piperazine, modifications to the standard preparative procedure were needed because either one or both of the amine functions can be involved in salt formation. The salt with two piperazines per molybdenum, i.e., $(Piperazine)_2 H_2MoS_4$, was favored with higher piperazine/Mo ratios in the reaction mixture, e.g., 250 g. piperazine per 100 g. of APM and 1 l water at digestion temperatures of 65°–85° C. With 100 g. of piperazine under such conditions, $(Piperazine)_1 H_2MoS_4$ was formed with digestion temperatures of 65°–85° C., while a previously unreported oxythiomolybdate was formed at a low digestion temperature, e.g., less than 10° C. A fourth piperazine-containing product was prepared by substituting piperazine for ammonia in the recipe for the elevated temperature and pressure synthesis of the ammonium salts of molybdenumsulfur cluster anions as disclosed in the Kurtak, et al. patent, U.S. Pat. No. 3,876,755. This material is referred to herein as "autoclaved piperazine product."

Hexamethylenetetramine thiomolybdate was prepared by the procedures of Udupa, et al., Curr. Sci. 42, 676 (1973) and of Dembicka, et al., Rocz. Chem. 49, 1475 (1975). Both syntheses involved the treatment of hexamethylene-tetramine molybdate solutions with hydrogen sulfide. Using hydrazine as the salt, hydrazinium thiomolybdate, $(N_2H_4)_2H_2MoS_4$, was prepared by the method of Udupa, et al. The tetramethyl-ammonium hydroxide salt proved difficult to prepare reproducibly as a result of mixed phases, poorly crystalline products, and/or low yields. An acceptable, but not optimum, procedure consisted of treating a solution consisting of 150 g of tetramethylammonium hydroxide pentahydrate, 20 g of molybdenum trioxide and 500 ml of water with $H_2S$ at less than 10° C.

The thiomolybdate salts of the invention were converted to $MoS_2$ products, or doped variations thereof, by heating said salts to a decomposition temperature of 400°–500° C., with the salts being heated at a rate within the range of from about 0.5° to 2° C., in an essentially oxygen-free atmosphere, i.e., under vacuum, through the relatively narrow temperature range or interval at which the salt essentially decomposes and a majority of its weight is lost. Further heating to the indicated decomposition temperature assured that the decomposition was complete, and the retention of residual sulfur was avoided. The salts were held at decomposition temperature for 1–3 hours, then cooled to room temperature either under nitrogen or $H_2$/argon. Air was introduced gradually at room temperature by incremental air/nitrogen mixture. The $MoS_2$ thus produced was pelletized for catalytic evaluation by either pressing into ⅛" diameter×⅛" long cylinders, or by forming ½" diameter×¾" cylinders that were subsequently crushed and sized to 10/20 mesh.

Catalysts prepared in accordance with the invention have been evaluated in a tubular reactor under varying conditions of temperature, pressure, $CO:H_2$ ratio and gas hourly space velocity (SV in hr.$^{-1}$). Conditions of 400° C. outlet temperature, 400 psig, $CO:H_2$ ratios of 1:3 and SV of 3300 hr.$^{-1}$ were most commonly employed. The advantages of the invention were demonstrated by comparing performance data obtained by means of $MoS_2$ prepared in accordance with the invention with $MoS_2$ prepared by methods believed representative of the prior art teachings as indicated above. The reactor employed was a one cm. I.D. reactor containing approximately 15 ml., typically about 20 grams, of catalyst, a back-pressure regulator that maintained the system at a preset constant pressure, a differential flow controller-needle valve combination that maintained a constant flow into the system, and an on-line gas chromatograph and wet test meter to monitor the composition and volume of the product stream. The reactor was mounted vertically in an 8" Lindberg clamshell furnace having a 1" bore. The temperature of the reactor was maintained with a West SCR Stepless Controller via a thermocouple attached to the outside of the reactor. Catalyst temperature was measured by a second thermocouple mounted axially in the reactor with the tip about one cm. from the bottom of the bed. The sulfide catalysts were significantly more active for the water gas shift reaction, i.e., reaction (2), than for methanation, i.e., reaction (1). Reflecting this, two measures of catalyst performance were used for evaluation purposes. These were (a) the percent of the CO fed to the system that was converted to hydrocarbons, e.g., methane, ethane, propane, and (b) total CO conversion, i.e., the amount of CO converted to hydrocarbons plus the amount consumed by the shift reaction. Surface areas were determined by a single point BET method using a Quantachrom Monosorb Analyzer. The catalytic performance of the various $MoS_2$ types is summarized in the table below:

TABLE

Catalytic Performance

| Catalyst Type | Initial Performance[a] % CO to Hydrocarbons | % CO Conv. | After Overnight Operation % CO to Hydrocarbons | % CO Conv. |
|---|---|---|---|---|
| 1. Commercial $MoS_2$ | nil | nil | — | — |
| 2. Sulfided Ammonium Paramolybdate (APM) | 36 | 63 | — | — |
| 3. Sulfided $MoO_3/Al_2O_3$ | 48 | 82 | — | — |
| 4. Sulfided Climax Mo—$MoO_2$ | 30 | 54 | — | — |
| 5. $(Piperazine)_2H_2MoS_4$ | 69 | 94 | 68 | 93 |
| 6. $(Piperazine)H_2MoS_4$ | 58 | 87 | 59 | 88 |
| 7. $(Piperazine)H_2MoOS_3$ | 66 | 93 | 60 | 88 |
| 8. $(Piperazine)_2H_2MoS_4$ | 58 | 87 | 59 | 88 |
| 9. $(Pyrrolidine)_2H_2MoOS_3$ | 61 | 90 | 57 | 87 |
| 10. $(n-Butylamine)_2H_2MoS_4$ | 66 | 93 | 56 | 85 |
| 11. $(Diethylamine)_2H_2MoS_4$ | 67 | 93 | 60 | 86 |
| 12. Autoclaved Piperazine Product | 71 | 95 | 59 | 86 |
| 13. Tetramethylammonium Thiomolybdate | 67 | 96 | 67 | 96 |

[a]400° C. outlet; 400 psig; $CO:H_{2-1}$ = 1:3; Space Velocity; SV - 3000 hr. except that catalyst type 5 was tested at 500° C.

As can be seen from the results both for total CO conversion, i.e., water gas shift plus methanation, and the conversion of CO to hydrocarbons, i.e., methane plus smaller amounts of higher paraffins, in the Table, the state-of-the-art catalysts, i.e., catalysts 1–4, were markedly inferior to the $MoS_2$ catalysts of the invention, i.e., catalysts 5–13, prepared by the decomposition of selected substituted ammonium thiomolybdate salts in accordance with the invention. In general, the activities and stabilities of the amine-derived samples were remarkably similar considering the wide range of structure types, composition and basicity represented in the parent amines. Although many of the $MoS_2$ catalyst materials prepared had a high surface area, the product from catalyst type 7, i.e., piperazinium oxythiomolybdate, had a very low surface area of only 5 m²/gm but nevertheless had a very respectable activity.

In the practice of the invention, various modifications can be employed to enhance the stability of the catalyst. Such modifications include decomposing the substituted ammonium thiomolybdate salt in admixture with an inert, preformed particulate diluent, bulk doping the thiomolybdate salt, as with tungsten or vanadium, prior to decomposition, or mixing the $MoS_2$ catalyst product with a suitable catalyst support additive, and suitable binders as required, for desired support and/or dispersion of the active catalyst material. By means of such modifications, catalyst life may be extended by retarding the effects of sintering that lead to a decrease in the amount of exposed catalyst surface, which, in turn, leads to a decrease in catalytic activity.

As an example of the decomposition of the substituted ammonium thiomolybdate salt in admixture with an inert, preformed particulate diluent, a preformed colloidal $ZrO_2$ can be added to the selected substituted ammonium thiomolybdate salt preparation, followed by the indicated thermal decomposition of the invention, to produce a matrixed $MoS_2$, i.e., a $MoS_2$-$ZrO_2$ material, having comparable activity and some improvement in long-term stability as compared with $MoS_2$ product not so matrixed. A cubic yttria-stabilized zirconia, prepared by the process disclosed in U.S. Pat. No. 4,065,544, can be employed in slurry form for this purpose. Silica can also be employed as another example of a suitable inert, preformed particulate diluent.

$MoS_2$ prepared in accordance with the invention can also be bulk doped with tungsten or vanadium to achieve desirable stability characteristics in the $MoS_2$ catalyst product. The tungsten doped $MoS_2$ obtained by decomposing a doped, Mo-containing salt of the above formula is $Mo_yW_{1-y}S_2$, where y is generally from about 0.5 to about 0.9. Similarly, replacement of some of the substituted ammonium thiomolybdate salt by $V_2O_5$ leads to mixed Mo-V thiosalts from which vanadium doped products having the formula $Mo_yV_{1-y}S_2$, where y is likewise generally from about 0.5 to about 0.9.

It will be appreciated that it is also within the scope of the invention to support the $MoS_2$ catalyst material on a preformed, porous carrier. For this purpose, various catalyst support and/or dispersion materials, such as alumina, silica, zirconia, thoria, and mixtures thereof, may be considered, with such carriers being employed in a wide variety of concentrations, e.g., from about 10% to about 90% by weight based on the overall weight of catalyst and carrier as in the use of matrixed $MoS_2$ products. Those skilled in the art will appreciate that not all of the commercially available, preformed, porous carrier materials are suitable for application to the $MoS_2$ catalyst system of the invention. The carrier would thus be selected on an overall technical-economic evaluation basis in light of the activity and stability characteristics provided thereby.

The decomposition products of the invention have the approximate composition $MoS_2$, but departures from ideal stoichiometry may occur as a result of (a) incomplete removal of sulfur during catalyst preparation, resulting in S:Mo ratios of greater than two, (b) oxidation of the catalyst surfaces when exposed to moist air, or (c) slow changes that may occur during catalytic use, such as the formation of Mo and $H_2S$ by reaction of $MoS_2$ with hydrogen, or the formation of $MoO_2$ and $H_2S$ by the reaction of $MoS_2$ with water.

Changes in stoichiometry resulting from effects (a) and (b) and falling within the S:Mo range of 1.5–2.5:1 appear to have little influence on catalytic performance. Long-term changes as a result of effect (c) are avoidable by maintaining the $H_2S:H_2$ and $H_2S:H_2O$ ratios in the reactor greater than $10^{-6}:1$ and $10^{-4}:1$, respectively. In general, it appears that, after a very short break-in period, catalytic activity appears quite insensitive to any of the indicated variations from ideal $MoS_2$ stoichiometry. For practical commercial operations, the feed gas for water gas shift and methanation activities using the sulfur-resistant $MoS_2$ catalyst of the invention can be that generated in a variety of commercial operations, such as (1) various coal gasification processes known in the art, (2) waste disposal systems, e.g., the Union Carbide Corporation PUROX TM System for high temperature incineration and pyrolysis of refuse, and (3) metallurgical operations such as blast furnaces, phosphorous furnaces, metal carbide furnaces and the like. The effluent gases from such operations will normally contain CO and $H_2$, generally within the molecular ratio range of 1:1–1:3, diluents, such as $CO_2$, $N_2$ and $H_2O$, and potential poisons such as $H_2S$. The $MoS_2$ catalysts of the invention operate successfully across a wide range of feed compositions. The tolerable $H_2S$ level can vary from a few ppm to several percent, with the active $MoS_2$ catalyst of the invention having the advantage that the higher levels of $H_2S$ content in the feed gas do not effectively destroy its activity as occurs in the use of other, less sulfur-resistant, methanation catalyst materials. As water is a mild inhibitor, preferred feeds to the catalyst will avoid unnecessary steam addition over that needed from stoichiometric considerations. In practice, the actual feed composition to the catalyst will be determined by various pertinent factors such as the optimum balance between available feed compositions, extent of steam addition required and recycle ratios. The $MoS_2$ catalyst can be employed in any suitable form, as for example in pelleted form in a fixed-bed reactor, with conversion to more attrition-resistant form as hereinabove indicated and with appropriate use of inert, conventional binders as desired, or in finely divided form in a fluidized bed or liquid slurry reactor.

The molybdenum sulfide catalysts prepared under the controlled thermal decomposition conditions of the invention have also been found desirable for use in catalyzed hydrogenation and hydrotreating reactions. For such applications, molybdenum oxides have commonly been converted to the sulfide form prior to or during use, with the molybdenum sulfide being supported on a $\gamma$-alumina carrier. Cobalt and/or nickel sulfide is also present as a promoter. Cobalt and/or nickel-promoted $MoS_2$ catalysts prepared by the thiosalt precursor method of the invention have been found to have significantly higher activity than existing commercial products.

The hydrodenitrogenation activity of the $MoS_2$ catalysts of the invention for petroleum feedstock can be demonstrated by preparing such catalysts, in conventional nickel promoted form, using the selected substituted thiomolybdate salt, nickel acetate, $Ni(Ac)_2.4H_2O$, $NH_4OH$ and water. The nickel acetate, ammonium hydroxide and water can be combined, and the selected salt added thereto. The mixture can then be cooled, as in an ice bath, and $H_2S$ can then be bubbled therein until consumption of $H_2S$, and precipitation of NiS, ceases. The precipitate can be filtered, washed with denatured alcohol and dried, e.g., at 80° C. overnight. The combined powders thus obtained can be blended in a mill, mixed by rolling, pelletized and then reduced with very slow heating, e.g., at a rate of between about 0.5° and about 2° C., in a carefully controlled non-oxygen atmosphere, as by vacuum or other suitable means, in the temperature interval in which a substantial portion of the substituted thiomolybdate salt decomposes.

The desirable hydrotreating, i.e. hydrodesulfurization and/or hydrodenitrogenation, and hydrogenation activities of the $MoS_2$ product of the invention, particularly when employed in nickel or cobalt-promoted form, will readily be appreciated in practical commercial operations. It will be understood that the promoted catalysts can be prepared from the selected substituted ammonium thiomolybdate salts by various impregnation and precipitation procedures falling within the scope of the invention as herein disclosed and claimed.

As indicated above, it is convenient to form the nickel or cobalt-promoted catalyst by precipitating NiS or CoS in the presence of a selected ammonium thiomolybdate salt, and thereafter thermally treating the mixture to convert the substituted ammonium thiomolybdate salt to the highly desirable form of MoS$_2$ produced in the recited process. The nickel or cobalt-promoted catalysts can be prepared with various amounts of nickel or cobalt present for the intended purpose as is known in the art. It should be noted that nickel or cobalt acetates have been added to reaction mixtures in amounts corresponding to a promoter/molybdenum mole ratio of 0.4 for maximum hydrodesulfurization activity in operations utilizing prior art MoS$_2$ catalyst compositions.

While catalysts have been employed in an unsupported, undiluted form in various hydrotreating evaluation applications, it will be appreciated that the commercial aspects of hydrotreating activities will likely require that a support catalyst, e.g., a $\gamma$-alumina support, be employed, as in conventional operations, to maintain catalyst costs comparable to existing products in continuous commercial operations. Since hydrogen is relatively expensive, the amount consumed is another important factor in the economics of commercial hydrotreating operations. Ideally, consumption would be limited to the amount of hydrogen needed to react with the constituents constituting heteroatoms, but, in practice, it has been found that additional hydrogen is consumed in the hydrogenation of multiple ring aromatic compounds that contain no hetero-atoms. The hydrogenation activity of the MoS$_2$ catalysts of the invention is demonstrated thereby and can be further demonstrated by the use of such catalysts, in promoted and unpromoted form, in the hydrogenation of representative feedstocks, such as methyl-naphthalene.

The improved hydrodesulfurization and hydrodenitrogenation of liquid fuels will be needed when it becomes necessary to process lower grade petroleum feedstocks and the alternate fuel sources, such as liquefied coal, shale oil, tar sands, and the like, that are under consideration as replacements for petroleum. The MoS$_2$ catalysts prepared in accordance with the invention are of significance, therefore, in a number of highly important applications related to the ever-growing search of new and improved technologies for meeting the energy and chemical feedstock requirements of industrial societies.

What is claimed is:

1. A process for the production of improved, sulfur resistant catalysts comprising thermally decomposing a thiomolybdate salt having the formula B$_2$[MoO$_x$S$_{4-x}$], where B is a substituted aliphatic ammonium or a cyclic amine containing one or more basic N atoms, and x is 0, 1 or 2, at a decomposition temperature of from about 300° C. to about 800° C., said substituted ammonium thiomolybdate salt being heated to said decomposition temperature slowly, in an essentially oxygen-free atmosphere, through the temperature interval in which a substantial portion of said substituted ammonium thiomolybdate salt decomposes, said salt decomposing to form a molybdenum disulfide, MoS$_2$, product having desirable properties for use as a catalyst for water gas shift and methanation reactions and for catalyzed hydrogenation or hydrotreating reactions.

2. The process of claim 1 in which said salt is decomposed at a temperature of from about 400° C. to about 500° C.

3. The process of claim 1 in which said molybdenum disulfide has a surface area of from about 25 to about 150 m$^2$/gm.

4. The process of claim 1 in which said ammonium thiomolybdate salt is heated to said decomposition temperature slowly, at a rate of about 0.5° to about 2° C./min., under vacuum, through said temperature interval in which a substantial portion of the substituted ammonium thiomolybdate salt decomposes.

5. The process of claim 1 in which B is the piperazinium cation.

6. The process of claim 1 in which B is the hexamethylenetetramonium cation.

7. The process of claim 1 in which B is n-C$_4$H$_9$NH$_3^+$.

8. The process of claim 1 in which said B is (C$_2$H$_5$)$_2$NH$_2^+$.

9. The process of claim 1 in which said B is (CH$_3$)$_4$N$^+$.

10. The process of claim 1 in which said B is the piperidinium cation.

11. The process of claim 1 in which said B is the pyrrolidinium cation.

12. The process of claim 1 and including decomposing said thiomolybdate in admixture with an inert, preformed particulate diluent, the stability of the resulting MoS$_2$ product being improved thereby.

13. The process of claim 4 in which said salt is decomposed at a temperature of from about 400° C. to about 500° C., the resulting molybdenum disulfide has a surface area of from about 25 to about 150 m$^2$/gm.

14. The process of claim 5 in which x is 0, said salt being piperazinium thiomolybdate.

15. The process of claim 5 in which x is 1, said salt being oxythiomolybdate.

16. The process of claim 14 in which said salt is decomposed at a temperature of from about 400° C. to about 500° C.

17. The process of claim 15 in which said salt is decomposed at a temperature of from about 400° C. to about 500° C.

18. An improved, sulfur resistant catalyst produced by the process comprising thermally decomposing a thiomolybdate salt having the formula B$_2$[MoO$_x$S$_{4-x}$], where B is a substituted aliphatic ammonium ion or a cyclic amine containing one or more basic N atoms, and x is 0, 1 or 2, at a decomposition temperature of from about 300° C. to about 800° C., said substituted ammonium thiomolybdate salt being heated to the decomposition temperature slowly, in an essentially oxygen-free atmosphere, through the temperature interval in which molybdate salt decomposes, said salt decomposing to form a molybdenum disulfide, MoS$_2$, product having desirable properties for use as a catalyst for water gas shift and methanation reactions and for catalyzed hydrogenation or hydrotreating reactions.

19. The catalyst of claim 18 in which said decomposition temperature is from about 400° C. to about 500° C., said product molybdenum disulfide having a surface area of from about 25 to about 150 m$^2$/gm.

20. The catalyst of claim 18 in which said salt is heated slowly, at a rate of from about 0.5 to about 2° C./min., under vacuum, through said temperature interval in which the substantial portion of said substituted salt decomposes.

21. The catalyst of claim 18 in which B is the piperazinium cation.

22. The catalyst of claim 18 in which B is the hexamethylenetetramonium cation.

23. The catalyst of claim 18 in which said B is n-$C_4H_9NH_3^+$.

24. The catalyst of claim 18 in which said B is $(C_2H_5)_2NH_2^+$.

25. The catalyst of claim 18 in which said B is $(CH_3)_4N^+$.

26. The catalyst of claim 18 in which said B is the piperidinium cation.

27. The catalyst of claim 18 in which said B is the pyrrolidinium cation.

28. The catalyst of claim 19 in which said salt is heated slowly, at a rate of from about 0.5° to about 2° C./min., under vacuum, through said temperature interval in which the substantial portion of said substituted salt decomposes.

29. The catalyst of claim 21 in which x is 0, said salt being piperazinium thiomolybdate.

30. The catalyst of claim 21 in which x is 1, said salt being piperazinium oxythiomolybdate.

* * * * *

UNITED STATES PATENT AND TRADEMARK OFFICE
CERTIFICATE OF CORRECTION

PATENT NO. : 4,243,553
DATED : January 6, 1981
INVENTOR(S) : A. W. Naumann, et al.

It is certified that error appears in the above—identified patent and that said Letters Patent is hereby corrected as shown below:

At column 1, line 37, "absorben" should read -- absorbent --.

At column 7, line 2, "molybdenumsulfur" should read -- molybdenum-sulfur --.

At column 8, line 29, "8.(Piperazine)$_2$H$_2$MoS$_4$" should read -- 8.(Piperidine)$_2$H$_2$MoS$_4$ --.

Signed and Sealed this

Sixteenth Day of June 1981

[SEAL]

Attest:

RENE D. TEGTMEYER

Attesting Officer

Acting Commissioner of Patents and Trademarks